United States Patent
Yoshikawa et al.

(10) Patent No.: US 8,437,003 B2
(45) Date of Patent: May 7, 2013

(54) INFORMATION PROCESSING APPARATUS AND METHOD

(75) Inventors: Hiroshi Yoshikawa, Kawasaki (JP); Yusuke Mitarai, Tokyo (JP); Masafumi Takimoto, Pittsburgh, PA (US); Kazuyuki Ota, Yokohama (JP); Kenji Saitoh, Tokyo (JP); Masakazu Matsugu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 284 days.

(21) Appl. No.: 12/812,008

(22) PCT Filed: Jan. 28, 2009

(86) PCT No.: PCT/JP2009/051829
§ 371 (c)(1),
(2), (4) Date: Oct. 27, 2010

(87) PCT Pub. No.: WO2009/096592
PCT Pub. Date: Aug. 6, 2009

(65) Prior Publication Data
US 2011/0037984 A1 Feb. 17, 2011

(30) Foreign Application Priority Data
Feb. 1, 2008 (JP) .................. 2008-022506

(51) Int. Cl.
*G01N 21/55* (2006.01)
(52) U.S. Cl.
USPC ....................................... 356/445; 356/237.1
(58) Field of Classification Search .......... 356/445–448, 356/600, 237.1–237.5
See application file for complete search history.

(56) References Cited

U.S. PATENT DOCUMENTS

| | | | | |
|---|---|---|---|---|
| 4,859,062 A | * | 8/1989 | Thurn et al. | 356/600 |
| 5,963,328 A | * | 10/1999 | Yoshida et al. | 356/600 |
| 6,088,117 A | * | 7/2000 | Imura et al. | 356/445 |
| 7,707,128 B2 | | 4/2010 | Matsugu | |
| 7,766,828 B2 | | 8/2010 | Ishii et al. | |
| 7,852,481 B2 | * | 12/2010 | Imura | 356/445 |
| 8,208,356 B2 | * | 6/2012 | Ishihara et al. | 369/53.1 |

(Continued)

FOREIGN PATENT DOCUMENTS

| | | |
|---|---|---|
| CN | 1696672 A | 11/2005 |
| EP | 0 580 909 A2 | 2/1994 |
| EP | 0580909 A2 | 2/1994 |
| JP | 2003-329586 A | 11/2003 |

OTHER PUBLICATIONS

Chinese Office Action dated Jul. 22, 2011 issued in corresponding Chinese Patent Application No. 200980103679.4.

(Continued)

*Primary Examiner* — Hoa Pham
(74) *Attorney, Agent, or Firm* — Fitzpatrick, Cella, Harper & Scinto

(57) ABSTRACT

An information processing apparatus includes an obtaining unit configured to obtain first information regarding a distribution of reflected light from a target to be measured and second information regarding geometrical-optics components of the reflected light, a calculating unit configured to calculate third information on the basis of the first information and the second information, the third information indicating an approximation of the distribution of reflected light, and an output unit configured to output information regarding wave-optics components of the reflected light on the basis of the third information.

8 Claims, 16 Drawing Sheets

U.S. PATENT DOCUMENTS

| | | | |
|---|---|---|---|
| 8,274,646 B2 * | 9/2012 | Ota et al. | 356/73 |
| 2005/0247895 A1 * | 11/2005 | Ando et al. | 250/559.44 |
| 2006/0092412 A1 | 5/2006 | Doshoda et al. | |
| 2007/0177233 A1 * | 8/2007 | Ichikawa et al. | 358/509 |
| 2007/0201029 A1 * | 8/2007 | Jinno | 356/446 |
| 2008/0211904 A1 | 9/2008 | Kato et al. | |
| 2010/0220338 A1 * | 9/2010 | Ota et al. | 356/601 |

OTHER PUBLICATIONS

Paolo Tomassini, et al., Novel Optical Sensor for the Measurement of Surface Texture, Review of Scientific Instruments, vol. 72, No. 4, pp. 2207-2213, Apr. 2001.

* cited by examiner

FIG. 5
(a) HIGH DIRECTIVITY
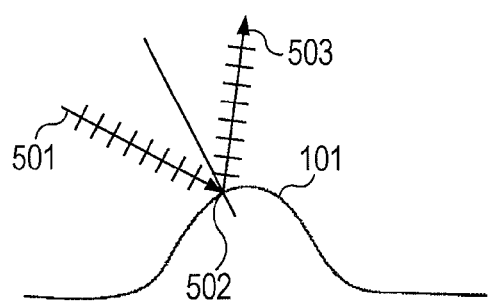
(c)
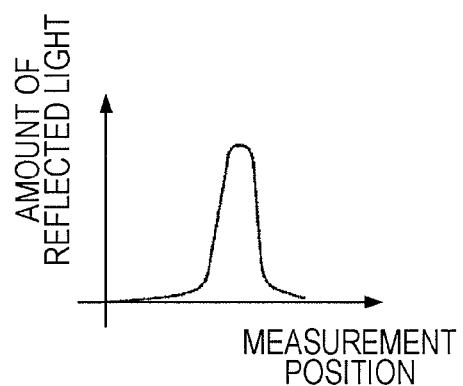
(b) LOW DIRECTIVITY
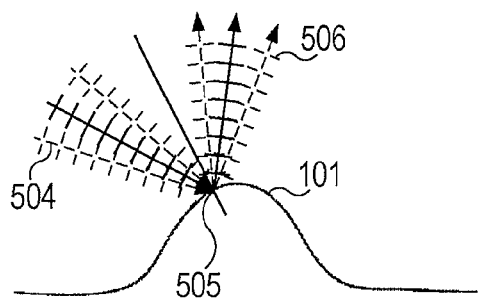
(d)
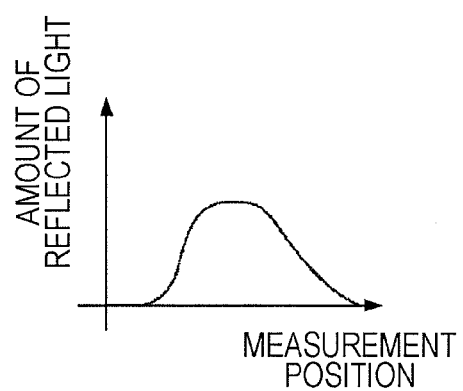

FIG. 12
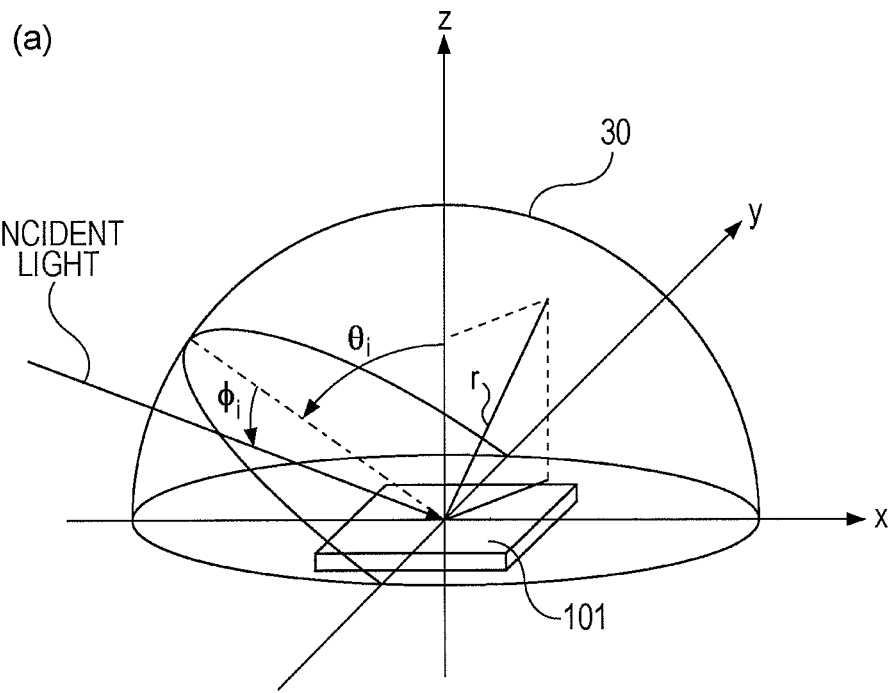
(a)
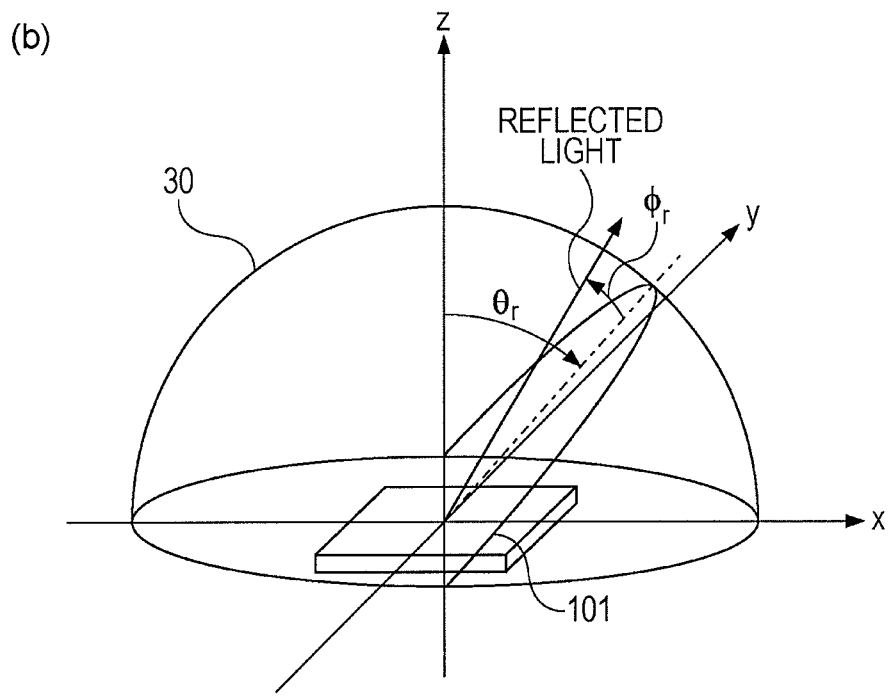
(b)

INFORMATION PROCESSING APPARATUS AND METHOD

This application is a National Stage application under 35 U.S.C. §371 of International Application No. PCT/JP2009/051829 filed on Jan. 28, 2009, which claims priority to Japanese Application No. 2008-022506, filed on Feb. 1, 2008, the contents of each of the foregoing applications being incorporated by reference herein.

TECHNICAL FIELD

The present invention relates to an apparatus and method for performing analysis of reflected light from a target to be measured.

BACKGROUND ART

With the use of a scattered light distribution formed by reflected light rays from a surface of an object, the texture of the object can be quantified. The quantification of texture allows the analysis regarding the glossiness of a printed surface or the like or the analysis of appearance of the object. With the application of scattered light distribution data to computer graphics, the appearance or texture of the object can be appropriately represented. Accordingly, scattered light distribution data may be widely applicable, and the scattered light distribution may be required in various situations. The classification of the scattered light distribution may be based on two types of scattered light.

The first type is scattered light originating from a surface having a structure whose size is substantially equal to or less than the wavelength of illumination light to be incident on a target object. If the wavelength of visible light ranges from 400 nm to 760 nm, the size of this structure may be about 760 nm or may be less than 760 nm although it depends on the wavelength of illumination light to be incident. The scattered light of this type depends on the surface roughness of a structure with a size on the order of the wavelength of the illumination light and the wavelength, and is typically derived from electromagnetic field analysis. In this specification, the scattered light of this type is hereinafter referred to as "scattered light or scatter caused by the wave-optics components".

The second type is scattered light originating from a surface having a structure whose size is greater than the wavelength of illumination light to be incident. The size of this structure may be about several micrometers to about several tens of micrometers or may be greater. The scattered light of this type is generated by diffuse reflection which depends on the angle of incidence of incident light and the inclination angle of the structure, and is derived from the general rule of reflection. The scattered light therefore does not depend on the wavelength of the illumination light but only depends on the structure of the surface of the object whose size is on the order greater than the wavelength of the illumination light. In this specification, the scattered light of this type is hereinafter referred to as "scattered light or scatter caused by the geometrical-optics components".

A technique for obtaining a scattered light distribution is disclosed in Patent Citation 1. In this technique, a parameter indicating a surface structure and an effective refractive index are used to estimate the relative-specular glossiness of the surface.

PATENT CITATION 1

Japanese Patent Laid-Open No. 2003-329586

DISCLOSURE OF INVENTION

Technical Problem

The texture of an object is determined by a combination of the scattered light caused by the wave-optics components and the scattered light caused by the geometrical-optics components. In the field of computer graphics, it may be necessary to modify only structural data that can affect the scattered light caused by the geometrical-optics components. Therefore, a demand exists for a simple method of separately obtaining the geometrical-optic and wave-optics components of scattered light.

In the estimation of the relative-specular glossiness disclosed in Patent Citation 1, the wave-optics and geometrical-optics components are taken into account. However, there is no disclosure of separate extraction of the wave-optics components from the geometrical-optics components.

The present invention provides a technique for easily obtaining information indicating wave-optics components of reflected light from a target to be measured.

Technical Solution

In an embodiment of the present invention, an information processing apparatus includes an obtaining unit configured to obtain first information regarding a distribution of reflected light from a target to be measured and second information regarding geometrical-optics components of the reflected light; a calculating unit configured to calculate third information on the basis of the first information and the second information, the third information indicating an approximation of the distribution of reflected light; and an output unit configured to output information regarding wave-optics components of the reflected light on the basis of the third information.

Advantageous Effects

According to an embodiment of the present invention, information indicating wave-optics components of reflected light from a target to be measured can be easily obtained.

BRIEF DESCRIPTION OF DRAWINGS

FIG. 5 is a diagram showing reflection in accordance with the directivity of illumination light.

FIG. 12 is a diagram showing a method of converting angular coordinates to rectangular coordinates according to the first embodiment.

BEST MODE FOR CARRYING OUT THE INVENTION

First Embodiment

Figure 1:
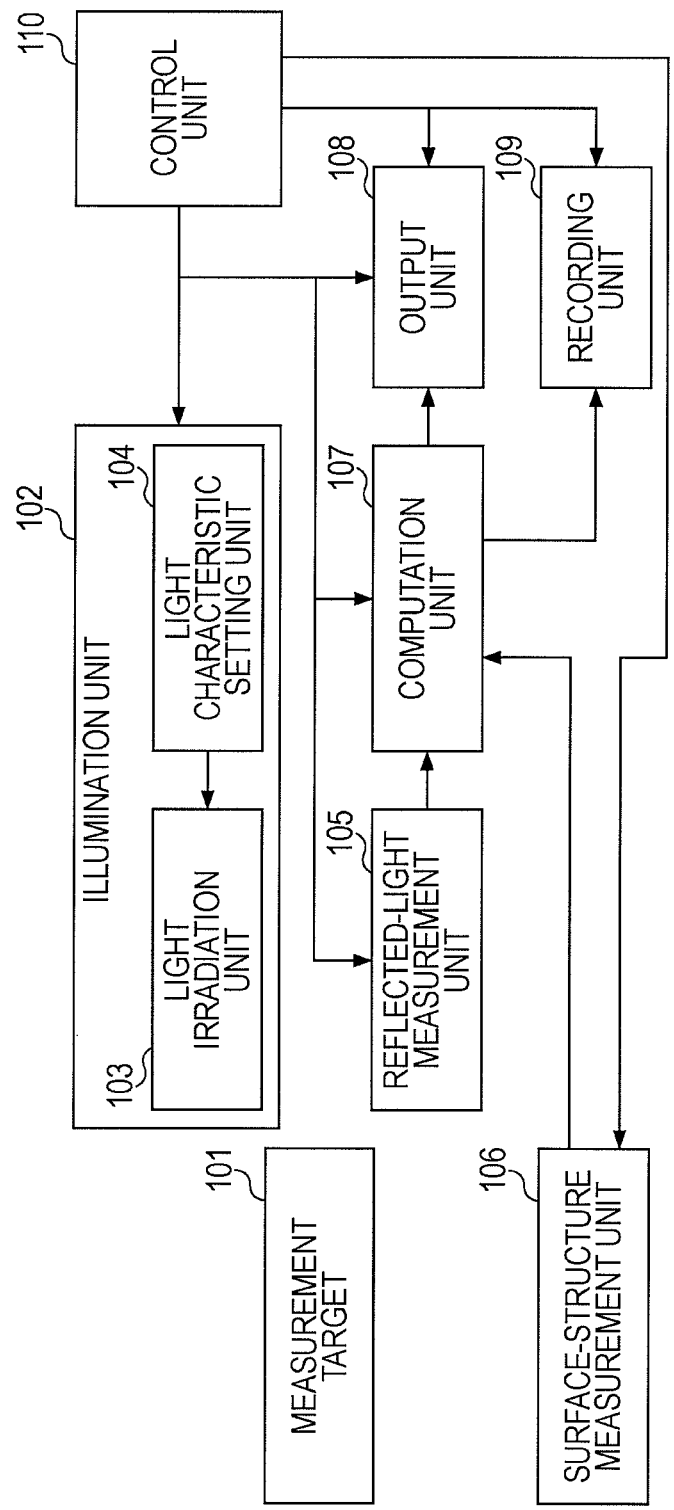
FIG. 1 is a block diagram of a measuring apparatus according to a first embodiment of the present invention.

FIG. 1 is a diagram showing a structure of a measuring apparatus according to a first embodiment of the present invention.

A measurement target 101 is an object to be measured using the measuring apparatus of the present embodiment.

The measurement target 101 may be, for example, a charging roller incorporated in a copying machine or the like, or a lens incorporated in a camera or the like. Any defect such as scratches on a surface may cause a product to malfunction, and therefore surface measurement is required.

An illumination unit 102 is a device configured to illuminate the measurement target 101.

The illumination unit 102 includes a light irradiation unit 103 that irradiates the measurement target 101 with light. The light irradiation unit 103 includes an electric lamp, a halogen lamp, and a xenon (Xe) strobe bulb.

A light characteristic setting unit 104 sets light characteristics of illumination light radiated from the light irradiation unit 103. The light characteristics are set based on a measurement request from a user or a macrostructure on a surface of the measurement target 101. The light characteristics are set in accordance with a measurement accuracy required for measurement of the measurement target 101. In the present embodiment, the light characteristics include the wavelength of the light, the polarization of the light, and the directivity of the light. The relationship between the measurement accuracy of a measurement target and the light characteristics of illumination light will now be described.

First, a description will be given of the wavelength of light, which is one of the light characteristics.

Figure 2:
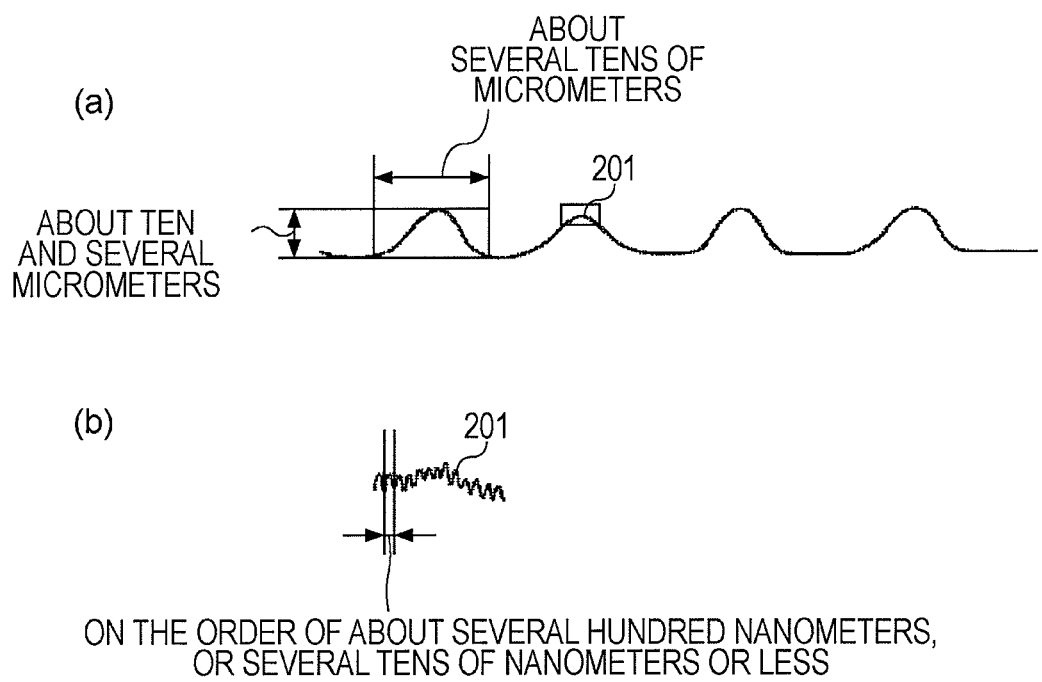
FIG. 2 is a diagram showing a surface structure of a measurement target.

FIG. 2 is a diagram showing a surface structure of the measurement target 101. In part (a) of FIG. 2, a surface structure of an object for inspection whose size is on the order greater than the wavelength of the illumination light is illustrated. As shown in part (a) of FIG. 2, the object for inspection generally has a large number of irregularities formed on a surface thereof. The irregularities shown in part (a) of FIG. 2 have a structure with a size of about ten and several micrometers to about several tens of micrometers. A reflecting surface with irregularities whose size is substantially equal to the wavelength of the light reveals the nature of waves of reflected light, and exhibits diffuse reflection. However, the wavelength of the light is about several hundred nanometers, and the irregularities shown in part (a) of FIG. 2 has no much effect on the scattering of the reflected light.

In part (b) of FIG. 2, a surface structure of the object for inspection whose size is substantially equal to the wavelength of the illumination light is illustrated. Part (b) of FIG. 2 is an enlarged scale view of the irregularities in a portion 201 of the surface structure shown in part (a) of FIG. 2. The irregularities shown in part (b) of FIG. 2 have a microstructure with a size of about several hundred nanometers, which is substantially equal to the wavelength of the light. Thus, light reflected from the irregularities shown in part (b) of FIG. 2 diffuses.

Figure 3:
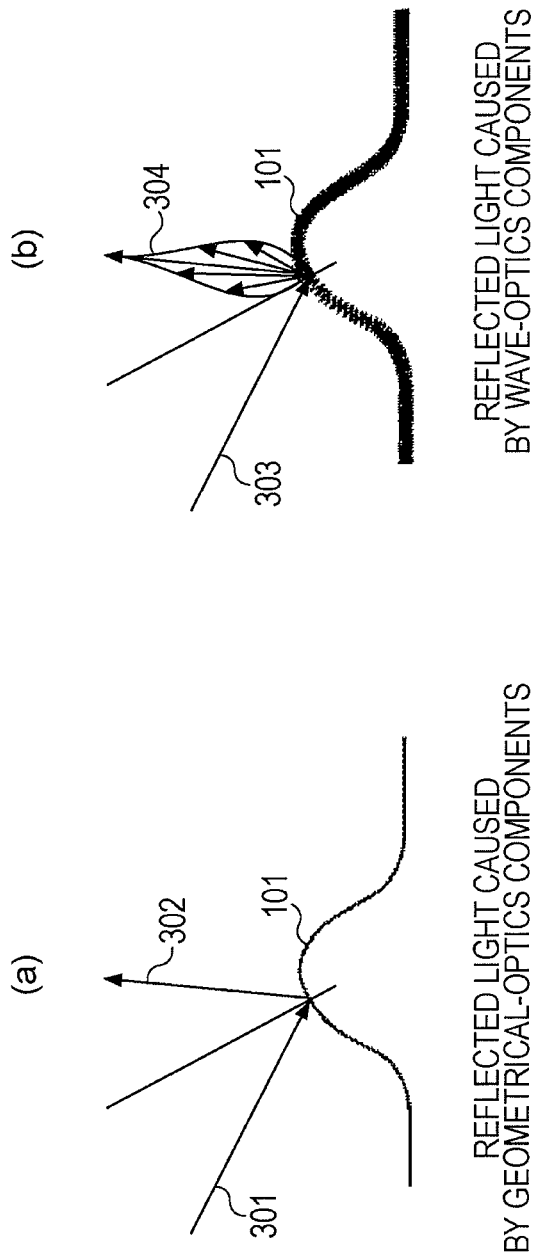
FIG. 3 is a diagram showing a relationship between the wavelength of illumination light and scattering of reflected light.

FIG. 3 is a diagram showing a relationship between the wavelength of illumination light and scattering of reflected light. Part (a) of FIG. 3 illustrates geometrical-optics components of reflected light 302 when the measurement target 101 is irradiated with illumination light 301. The geometrical-optics components of the reflected light 302 are reflected light components caused by a structure of the measurement target 101 whose size is about ten and several micrometers to about several tens of micrometers. The term "geometrical-optics components" originates because optical phenomena relating to the surface of the measurement target 101 can be explained by geometrical optics. As shown in part (a) of FIG. 3, the geometrical-optics components of the reflected light 302 are reflected regularly, called specular reflection.

Part (b) of FIG. 3 illustrates wave-optics components of reflected light 304 when the measurement target 101 is irradiated with illumination light 303. The wave-optics components of the reflected light 304 are reflected light components caused by a structure of the measurement target 101 whose size is about several hundred nanometers. The term "wave-optics components" originates because optical phenomena relating to the surface of the measurement target 101 can be explained by wave optics. As shown in part (b) of FIG. 3, the wave-optics components of the reflected light 304 are mainly reflected in directions other than the direction of specular reflection depending on the structure of the measurement target 101 whose size is about several hundred nanometers.

As described above, reflected light from the measurement target 101 varies in accordance with the relationship between the wavelength contained in irradiation light and the surface structure of the measurement target 101. The light characteristic setting unit 104 sets illumination light including a wavelength corresponding to the measurement accuracy.

Next, the polarization of light in the light characteristics will be described. The polarization of light represents the regularity in a direction in which light waves oscillate.

Figure 4:
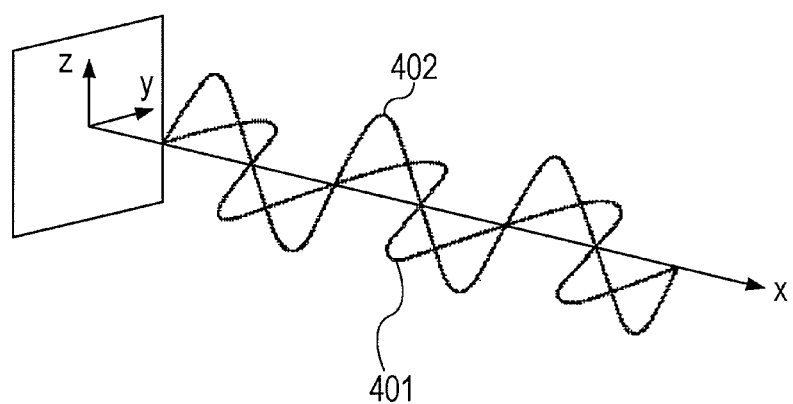
FIG. 4 is a diagram showing illumination light having waves in two oscillation directions.

FIG. 4 is a diagram showing illumination light having waves in two oscillation directions. In FIG. 4, the x axis represents the irradiation direction of the light.

An xy wave 401 represents an illumination light wave that oscillates on an xy plane shown in FIG. 4. An xz wave 402 represents an illumination light wave that oscillates on an xz plane shown in FIG. 4. The illumination light may further include illumination light waves that oscillate on planes other than the xy or xz plane. Illumination light actually includes a plurality of types of waves, and the intensity distribution of reflected light may vary depending on the types of waves included. The light characteristic setting unit 104 sets illumination light having a polarization corresponding to the measurement accuracy.

Finally, the directivity of light in the light characteristics will be described. The directivity of light represents the degree of spread of light radiated from the light irradiation unit 103. The higher directivity light has, the closer to parallel light the light is.

FIG. 5 is a diagram showing reflection in accordance with the directivity of illumination light.

In part (a) of FIG. 5, the measurement target 101 is irradiated with high-directivity illumination light. An illumination light ray 501 having a high directivity impinges at a point 502 on the measurement target 101. In the irradiation with high-directivity illumination light, the illumination light ray 501 impinging on the point 502 from a source of the illumination light ray 501 does not substantially diffuse in other directions. Therefore, the illumination light ray 501 impinging on the point 502 has a large amount of light in the same direction, and a reflected light ray 503 also has a large amount of light in the regular direction. The relationship between a measurement position and an amount of reflected light is shown in part (c) of FIG. 5.

In part (b) of FIG. 5, the measurement target 101 is irradiated with low-directivity illumination light. An illumination light ray 504 having a low directivity impinges at a point 505 on the measurement target 101. In the irradiation with low-directivity illumination light, the illumination light ray 504 impinging on the point 505 from a source of the illumination light ray 504 diffuses in other directions. Therefore, the illumination light ray 504 impinging on the point 505 has a large amount of light in different directions, and reflected light rays 506 diffuse. The relationship between a measurement position and an amount of reflected light is shown in part (d) of FIG. 5. The light characteristic setting unit 104 sets illumination light having a directivity corresponding to the structure of the measurement target 101. The light characteristic setting unit 104 performs light characteristic settings accordingly.

Referring back to FIG. 1, a reflected-light measurement unit 105 measures reflected light from the measurement target 101 to obtain reflected-light data. The reflected-light measurement unit 105 includes an optical sensor configured to detect reflected light from the measurement target 101. In the present embodiment, the reflected-light data may be represented by binarized image data or the like.

A surface-structure measurement unit 106 measures a surface structure of the measurement target 101. Examples of the surface structure of the measurement target 101 include irregularities formed on a surface of the measurement target 101. The surface-structure measurement unit 106 may be formed of a measuring device such as a laser microscope or a laser displacement meter, and performs measurement.

The surface structure of the measurement target 101 measured by the surface-structure measurement unit 106 has a shape which is on the order greater than the wavelength of the illumination light radiated from the light irradiation unit 103 or the reflected light measured by the reflected-light measurement unit 105. Alternatively, the surface-structure measurement unit 106 may be formed of a measuring device capable of measuring a structure with a size less than the order of the wavelength. For example, a measuring device capable of measuring a structure whose size is on the order equal to or less than the wavelength, such as an atomic force microscope (AFM) or a scanning electron microscope (SEM), may be used. When such a measuring device is used, the surface-structure measurement unit 106 performs a smoothing process on the obtained structural data to convert it into structural data whose size is on the order greater than the wavelength. The smoothing process may be performed by a computation unit 107 described below. In the present embodiment, the structural data may be represented by a three-dimensional coordinate value having a plurality of representative points on the surface of the measurement target 101.

The computation unit 107 calculates the reflected light caused by the wave-optics components using the structural data measured by the surface-structure measurement unit 106 and the reflected-light data measured by the reflected-light measurement unit 105. The computation unit 107 includes a graphics processing unit (GPU) and a video random access memory (VRAM), and the GPU analyzes the reflected-light data obtained by the reflected-light measurement unit 105 and the structural data obtained by the surface-structure measurement unit 106 which are stored in the VRAM. As a result of the analysis, the reflected light caused by the wave-optics components is calculated. A calculation method will be described below.

An output unit 108 outputs a computation result obtained by the computation unit 107. The output unit 108 includes a devices configured to display the computation result, such as a monitor or a printer.

A recording unit 109 is a device configured to record the computation result obtained by the computation unit 107. The recording unit 109 includes a device configured to record data of the computation result, such as a hard disk or a flash memory.

A control unit 110 controls the operation of the illumination unit 102, the reflected-light measurement unit 105, the surface-structure measurement unit 106, the computation unit 107, the output unit 108, and the recording unit 109. The control unit 110 includes a central processing unit (CPU), a RAM, and a read-only memory (ROM) having various control programs stored thereon.

The various programs stored on the ROM includes a control program for controlling the illumination unit 102 to radiate light, a control program for controlling the reflected-light measurement unit 105, and a control program for controlling the surface-structure measurement unit 106.

The various programs may further include a control program for controlling the computation unit 107, a control program for controlling the output unit 108, and a control program for controlling the recording unit 109. The measuring apparatus according to the present embodiment is configured as described above. Note that a portion of the configuration of the measuring apparatus shown in FIG. 1 may be replaced with a general personal computer or any other suitable device.

Next, the operation of the measuring apparatus according to the present embodiment will be described.

Figure 6:
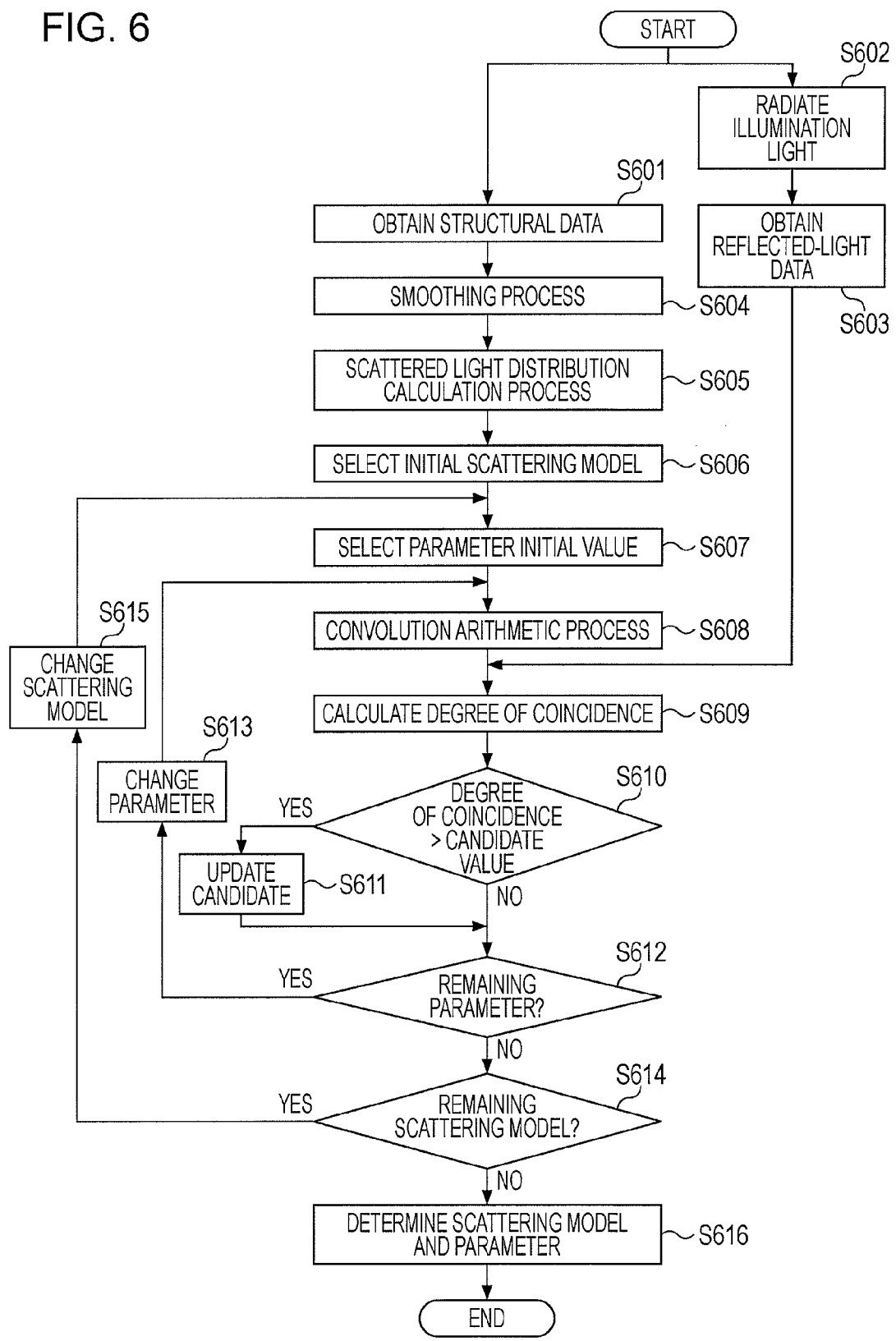
FIG. 6 is a flowchart showing a process performed by the measuring apparatus according to the first embodiment.

FIG. 6 is a diagram showing an exemplary process of the measuring apparatus according to the present embodiment. Steps of the process will now be described. The following process is a process of estimating the wave-optics components by using an approximation of a distribution of reflected light based on first information regarding the distribution of reflected light and second information regarding the geometrical-optics components.

In step S601, the control unit 110 causes the surface-structure measurement unit 106 to measure a surface structure of the measurement target 101 to obtain measurement information data. The processing of steps S602 and S603, which will be described below, may be performed in parallel to the processing of step S601 or may be performed after the processing of step S601.

In step S602, the control unit 110 controls the illumination of the illumination unit 102 to irradiate the measurement target 101 with illumination light. The control unit 110 controls light characteristics or the like of the illumination unit 102 to radiate illumination light suitable for measurement.

Alternatively, desired light characteristics may be set in response to an instruction given from a user instruction device (not shown).

In step S603, the control unit 110 causes the reflected-light measurement unit 105 to measure reflected light from the measurement target 101 to obtain reflected-light data indicating a luminance distribution.

In step S604, the computation unit 107 performs a smoothing process on the structural data obtained in step S601. The smoothing process is a process for removing measurement data that represents a structure whose size is about several hundred nanometers, which may contribute to the wave-optics components of the reflected light, to obtain data that may affect the geometrical-optics components. A variety of specific methods for the smoothing process have been proposed, such as a method using spline curves, which will not be discussed herein.

The smoothing process in step S604 may be performed by the surface-structure measurement unit 106 instead of the computation unit 107.

In step S605, the computation unit 107 calculates scattered light distribution functions indicating the geometrical-optics components of the reflected light on the basis of the measurement data subjected to the smoothing process in step S604.

Figure 7:
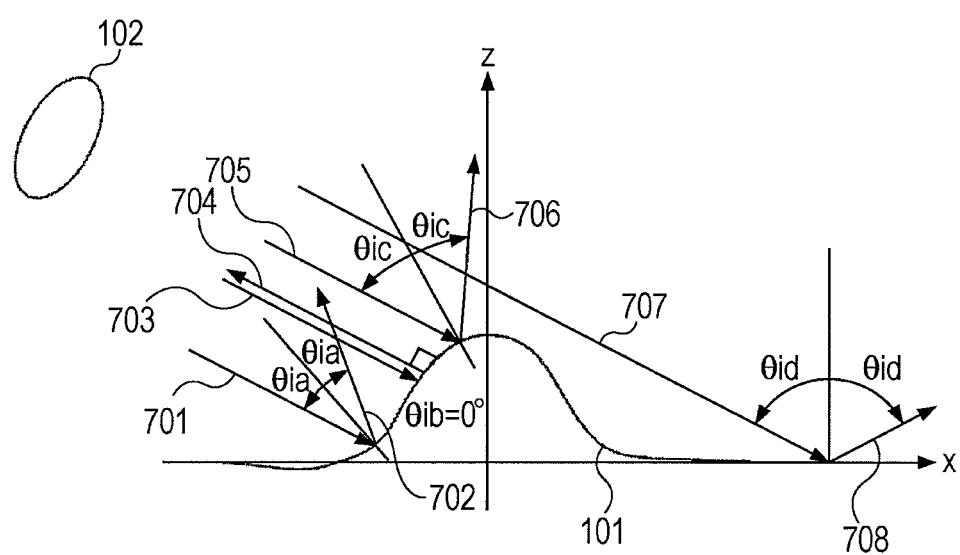
FIG. 7 is a diagram showing reflected light caused by the geometrical-optics components with respect to incident light.

FIG. 7 is a diagram showing reflected light rays 702, 704, 706, and 708 caused by the geometrical-optics components, which are obtained from incidence light rays 701, 703, 705, and 707. As shown in FIG. 7, if only the geometrical-optics components are taken into account, the incident light rays 701, 703, 705, and 707 and the reflected light rays 702, 704, 706, and 708 have a specular reflection relationship. Since only the specular reflection is taken into account, the scattered light distribution functions indicating the geometrical-optics components of reflected light can be easily calculated from the smoothed measurement data. The scattered light distribution functions are functions representing the distribution of the reflected light rays 702, 704, 706, and 708 based on the correspondence between the angles of the incident light rays 701, 703, 705, and 707 and the angles of the reflected light rays 702, 704, 706, and 708. A scattered light distribution function is generally represented by Equation (1) as follows:

$$\text{Geometrical-optics component of reflected light} = F_{cal}(\theta_i, \phi_i, \theta_r, \phi_r) \quad \text{Equation (1)}$$

where $\theta_i$ and $\phi_i$ are parameters representing the angle of incidence and $\theta_r$ and $\phi_r$ are parameters representing the angle of reflection. A given direction in a three-dimensional space can be represented using two angles. Thus, in order to represent the direction of each of an incident light ray and a reflected light ray in the three-dimensional space, each of the angle of incidence and the angle of reflection is assigned parameters that represent two angles.

Note that the distribution of the calculated scattered light distribution functions indicating the geometrical-optics components is different from a scattered light distribution of the reflected-light data obtained in step S603.

Figure 8:
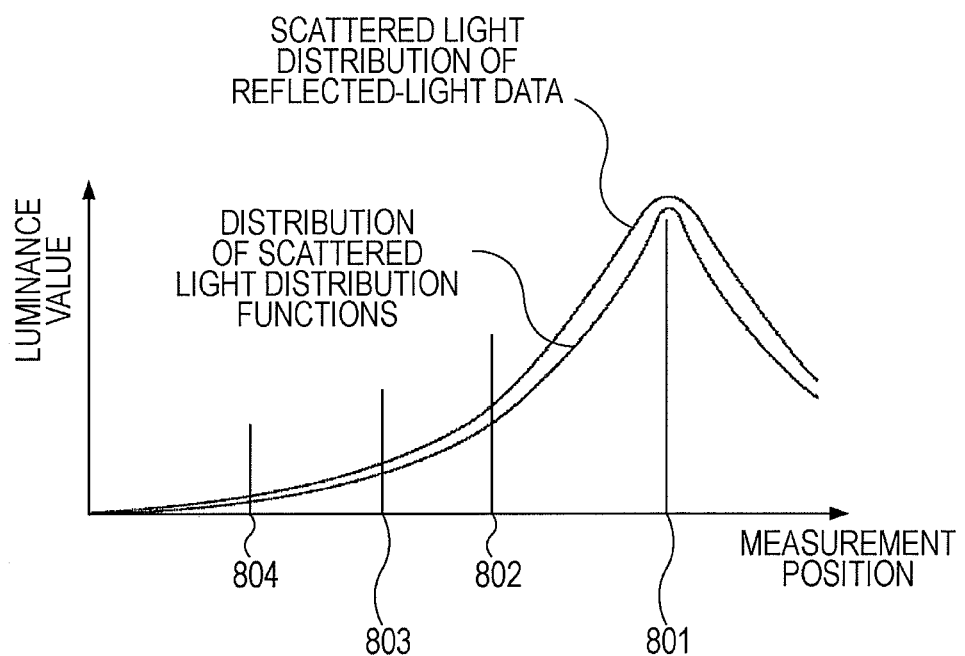
FIG. 8 is a diagram showing a relationship between a distribution of scattered light distribution functions representing the geometrical-optics components and a scattered light distribution of reflected-light data.

FIG. 8 is a diagram showing a relationship between the distribution of scattered light distribution functions indicating the geometrical-optics components and the scattered light distribution of the reflected-light data obtained in step S603. As shown in FIG. 8, substantially the same luminance value is obtained at a measurement position 801 where the positional relationship between the light irradiation unit 103 and the reflected-light measurement unit 105 is substantially equal to a specular reflection relationship. At measurement positions 802 to 803 where specular reflection does not occur, on the other hand, the scattered light distribution of the reflected-light data has greater luminance values. This is because the scattered light distribution of the reflected-light data contains the wave-optics components of the reflected light as well as the geometrical-optics components.

In step S606, the computation unit 107 selects an initial scattering model of the function indicating the distribution of reflected light caused by the wave-optics components. Preferably, a plurality of scattering models such as Gaussian scattering models and cos N-power scattering models may be provided as scattering models. Gaussian scattering models and cos N-power scattering models are bell-shaped models and are suitable to represent the distribution of reflected light caused by the wave-optics components. While the bell-shaped models are used in the present embodiment, other shaped models may be used. Here, a description will be given in the context of a Gaussian scattering model. A Gaussian scattering model can be represented by Equation (2) as follows:

[Math. 1]

$$P(\theta, \phi) = P_o \exp\left[\left(-\frac{1}{2}\right)\left(\frac{\theta}{\sigma_\theta}\right)^2\right] \exp\left[\left(-\frac{1}{2}\right)\left(\frac{\phi}{\sigma_\phi}\right)^2\right] \quad \text{Equation (2)}$$

In Equation (2), as $\sigma_\theta$ and $\sigma_\phi$ are varied, the model shape represented by Equation (2) also varies.

Figure 9:
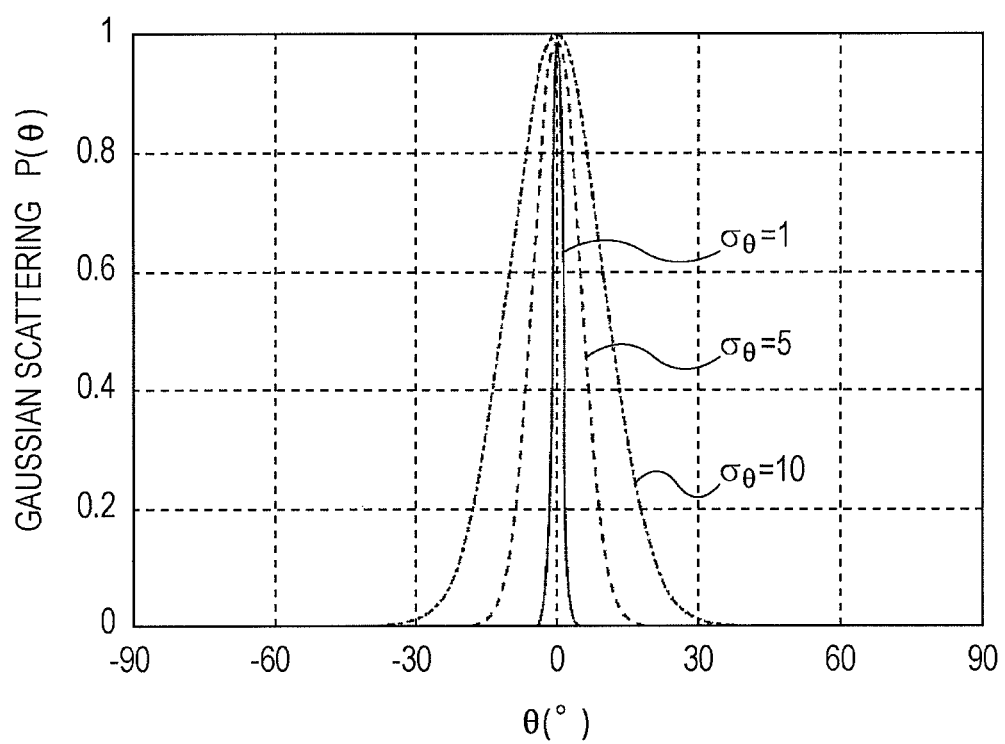
FIG. 9 is a diagram showing a one-dimensional model shape of a Gaussian scattering model with variations of a parameter $\sigma_\theta$.

FIG. 9 is a diagram showing a one-dimensional model shape with variations in the parameter $\sigma_\theta$ among the parameters $\sigma_\theta$ and $\sigma_\phi$. As shown in FIG. 9, the width of the bell shape increases with an increase in the parameter $\sigma_\theta$. With variations in the parameter $\sigma_\phi$, a two-dimensional model shape can also be changed.

Next, a cos N-power scattering model will be described. A cos N-power scattering model can be represented by Equation (3) as follows:

$$P(\theta, \phi) = P_0 \cos^{N\theta}(\theta) \cos^{N\phi}(\phi) \quad \text{Equation (3)}$$

Figure 10:
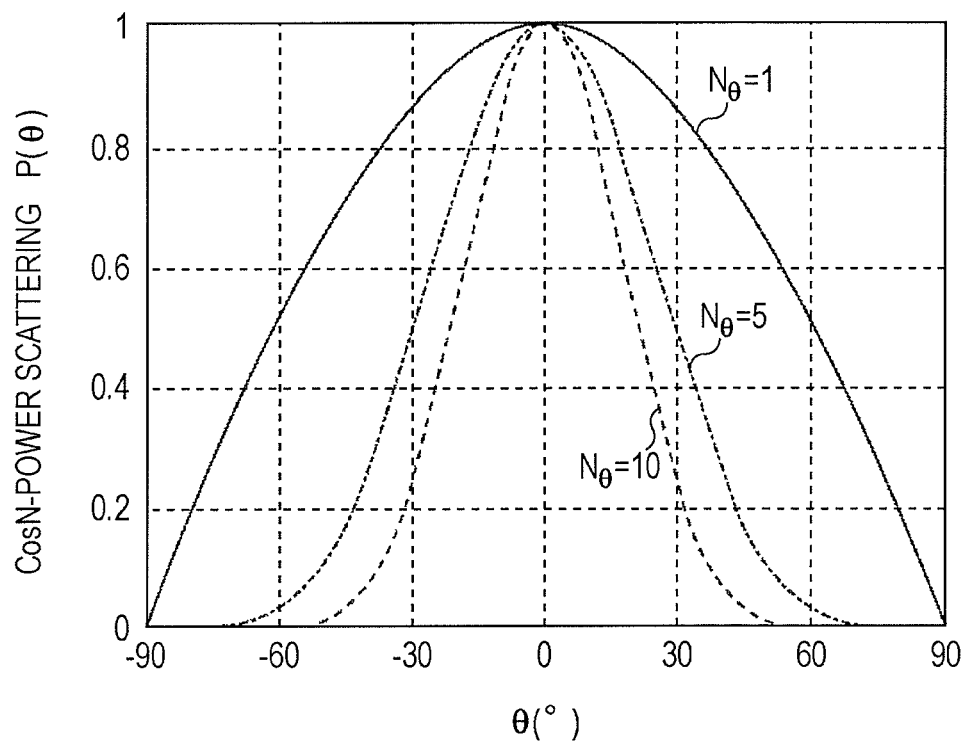
FIG. 10 is a diagram showing a one-dimensional model shape of a cos N-power scattering model with variations of a parameter $N_\theta$.

As the parameters $N_\theta$ and $N_\phi$ in Equation (3) are varied, the model shape represented by Equation (3) also varies. FIG. 10 is a diagram showing a one-dimensional model shape with variations in the parameter $N_\theta$ among the parameters $N_\theta$ and $N_\phi$. As shown in FIG. 10, the width of the bell shape is narrowed with an increase in the parameter $N_\theta$. With variations in the parameter $N_\phi$, a two-dimensional model shape can also be changed.

One of the models described above is selected to select an initial scattering model.

While the Gaussian scattering model or cos N-power scattering model is used in step S606, any other bell-shaped model may be used.

In step S607, the computation unit 107 sets an initial parameter value for the initial scattering model. For example, when the initial scattering model is a Gaussian scattering model, initial parameter values are set for the parameters $\sigma_\theta$ and $\sigma_\phi$. The value set as an initial parameter value, the range over which the parameter varies, the variation width of the parameter, and the like may be set as appropriate in accordance with an instruction from the user, system requirements, or any other matter.

In step S608, the computation unit 107 performs a convolution arithmetic process to calculate a composite function. The convolution arithmetic process is performed based on Equation (4) as follows:

[Math. 2]

$$F_{con}(\theta_i, \phi_i, \theta_r, \phi_r) = F_{cal}(\theta_i, \phi_i, \theta_r, \phi_r) \otimes P(\theta_r, \phi_r) \quad \text{Equation (4)}$$

Figure 11:
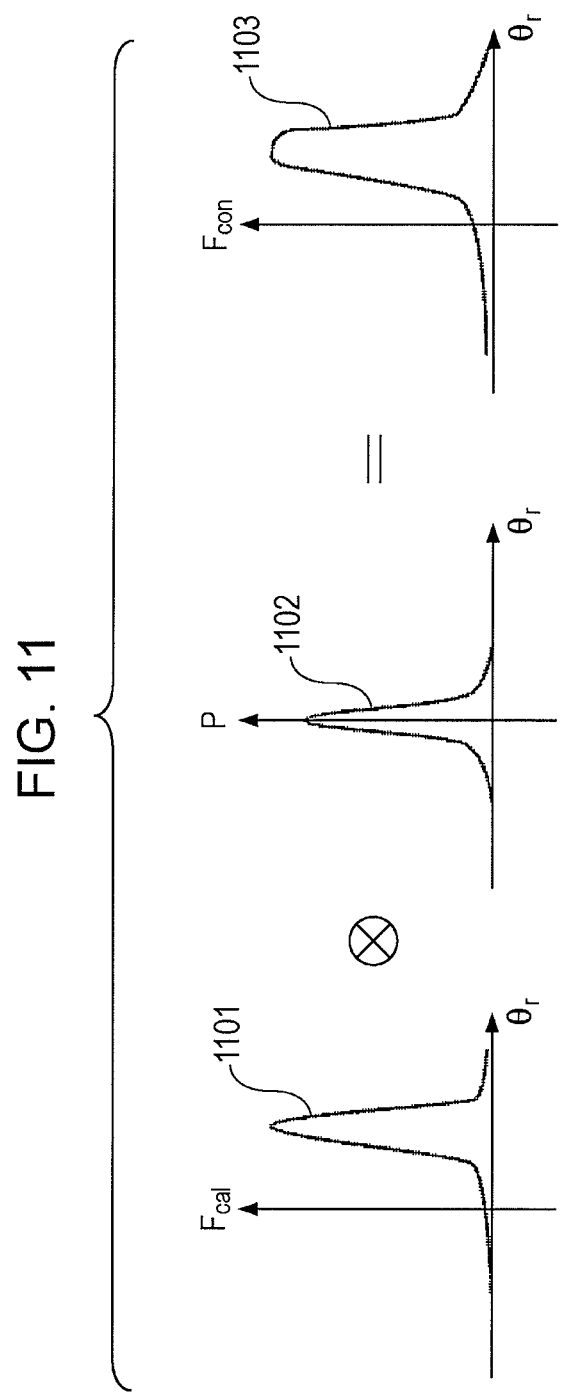
FIG. 11 is a diagram showing an overview of a convolution process.

FIG. 11 is a diagram showing an overview of the convolution process given by Equation (4).

Reference numeral 1101 denotes the distribution of functions representing the geometrical-optics components.

Reference numeral 1102 denotes the distribution of functions representing the wave-optics components.

Reference numeral 1103 denotes the combined distribution of composite functions generated by the convolution process. As shown in FIG. 11, the convolution of the functions 1101 representing the geometrical-optics components and the functions 1102 representing the wave-optics components yields the distribution of composite functions 1103 having the geometrical-optics components and the wave-optics components. In the present embodiment, the convolution process is accomplished by performing, for example, the convolution integral.

In step S609, the computation unit 107 calculates the degree of coincidence between the distribution of composite functions 1103 calculated in step S608 and the scattered light distribution of the reflected-light data. The calculation of the degree of coincidence is performed using Equation (5) as follows:

$$S = 1/|F_{mea}(\theta_i, \phi_i, \theta_r, \phi_r) - F_{con}(\theta_i, \phi_i, \theta_r, \phi_r)| \quad \text{Equation (5)}$$

where $F_{mea}$ denotes the function representing the scattered light distribution of the reflected-light data. In Equation (5), the value S, which represents the degree of coincidence, increases with an increase in the similarity between the distribution of composite functions and the scattered light distribution of the reflected-light data.

In step S610, the computation unit 107 determines whether or not the degree of coincidence calculated in step S609 is greater than a candidate value. The candidate value, as used herein, is the highest degree of coincidence among the degrees of coincidence previously calculated in step S609. If no degree of coincidence has yet been calculated, the candidate value is set to zero. If the degree of coincidence is greater than the candidate value, the composite function, which is used for the determination, can be regarded as being the most similar to the scattered light distribution of the reflected-light data among the previously calculated composite functions. Thus, if the degree of coincidence is greater than the candidate value as a result of the comparison therebetween, the process proceeds to step S611 to update the candidate value with the composite function. If the degree of coincidence is equal to or less than the candidate value, the process proceeds to step S612 to determine whether or not a remaining parameter value exists in order to apply another parameter.

In step S611, the computation unit 107 updates the candidate value used in step S610 with the composite function. The composite function used for the update processing of step S611 is a function that is determined in step S610 to exhibit the most similar distribution to the scattered light distribution of the reflected-light data among the composite functions. After the update processing, the process proceeds to step S612 to determine whether or not a remaining parameter value exists.

In step S612, the computation unit 107 determines whether or not a remaining parameter value exists. That is, it is determined whether or not any other parameter value that is applicable within the range over which the parameter varies, which is set in step S607, remains. The determination of whether or not any other applicable parameter value remains is performed based on information such as the variation width set in step S607 or the parameter value for which the determination has already been performed. If any parameter value remains, the process proceeds to step S613 to change the current parameter value to the remaining parameter value. If no remaining parameter values exist, the process proceeds to step S614 to determine whether or not a scattering model other than the currently set scattering model exists.

In step S613, the computation unit 107 changes the parameter value. That is, in step S613, the parameter value currently applied in the scattering model is updated to the remaining parameter value for which the determination in step S612 has been performed. After the parameter value has been updated in step S613, the process proceeds to step S608 to perform a convolution arithmetic process based on the scattering model with the updated parameter value.

In step S614, the computation unit 107 determines whether or not a remaining scattering model exists. That is, it is determined whether or not any applicable scattering model other than the scattering model that has been already applied exists. If any scattering model remains, the process proceeds to step S615 to change the currently applied scattering model to a remaining scattering model. If no remaining scattering models exist, the process proceeds to step S616.

In step S615, the computation unit 107 changes the scattering model. That is, in step S615, the currently applied scattering model is changed to the remaining scattering model determined in step S614. After the scattering model has been changed, the process proceeds to step S607 to set an initial parameter value for the function of the changed scattering model.

In step S616, the computation unit 107 determines a scattering model and a parameter that are suitable for the representation of scattered light on the surface of the measurement target 101. By repeating the loop of steps S607 to S614, a scattering model and a parameter that exhibit a scattered light distribution having the highest degree of coincidence in step S610 have been applied. Therefore, the scattering model and the parameter that are currently applied in step S616 are determined as a scattering model and a parameter that are suitable for the representation of scattered light on the surface of the measurement target 101. The determined scattering model and parameter are output to the output unit 108 or recorded on the recording unit 109.

According to the process described above, a distribution function that represents the approximation of the distribution of reflected light measured in step S603 can be obtained. The wave-optics components contained in the reflected light can also be estimated. The high-accuracy wave-optics components are required to reproduce, for example, the texture of an anisotropic material such as velvet, satin, or enamel by using computer graphics, and the estimation using the method described above would therefore be effective. Further advantageously, unlike contact-based measurement, the wave-optics components can be obtained without damaging the surface of the measurement target 101.

The data obtained in the process described above can be used for various types of analysis. For example, reflected light at a change in the shape of the measurement target 101 which is on the order greater than the wavelength of the illumination light can be simulated.

In the simulation process, first, if the surface structure includes a change on the order greater than the wavelength of the illumination light, the value $F_{cal}(\theta_i, \phi_i, \theta_r, \phi_r)$ is changed by reflecting the change of the surface structure of the measurement target 101. Reflecting the change of the structure only requires consideration of the specular reflections as shown in FIG. 7 and is readily achievable. Then, the convolution of the changed value $F_{cal}(\theta_i, \phi_i, \theta_r, \phi_r)$ and the scattering model representing the wave-optics components obtained in the process described above is performed. As a result of the convolution, a function representing reflected light from the measurement target 101 which involves a change in the structure on the order greater than the wavelength of the illumination light is calculated. Environmental conditions for the measurement target 101, such as illumination conditions and image pickup conditions, are set for the calculated function, thereby allowing simulation of the reflected light from the measurement target 101.

In the present embodiment, for simplicity of description, the scattered light distribution function given by Equation (1) is used. In general, however, a scattered light distribution function is defined by a function having five variables: the angle of incidence $\theta_i$, the azimuth angle of incidence $\phi_i$, the acceptance angle $\theta_r$, the acceptance azimuth angle $\phi_r$, and the incident light wavelength $\lambda$.

$$\text{Scattered light angular distribution} = F(\theta_i, \phi_i, \theta_r, \phi_r, \lambda) \quad \text{Equation (6)}$$

When the scattered light distribution function given by Equation (6) is used, it is necessary for the light characteristic setting unit 104 to set a certain wavelength and reflect the setting. By taking the wavelength components into account, higher-precision processing can be performed.

In the present embodiment, angles are used as arguments of the scattered light distribution function. In practice, a process using a rectangular coordinate system may often be performed.

FIG. 12 is a diagram showing a method of converting angular coordinates to rectangular coordinates according to the present embodiment. In parts (a) and (b) of FIG. 12, a relationship between angles represented by the angle of incidence $\theta_i$, the azimuth angle of incidence $\phi_i$, the acceptance angle $\theta_r$, and the acceptance azimuth angle $\phi_r$ and the xyz coordinates. As shown in part (a) of FIG. 12, the measurement target 101 is arranged so that a measurement surface of the measurement target 101 can be located in a plane parallel to the xy plane at a position given by z=0. Letting r be the radius of a hemisphere centered at an origin of the xyz coordinates, the relationship between the xyz coordinates and the parameters $\theta_i$, $\phi_i$, $\theta_r$, and $\phi_r$ is represented by Relations (7.1) and (7.2) as follows:

[Math. 3]

$$\begin{cases} x = r \cdot \sin\phi_i \\ y = r \cdot \sin\theta_i \cdot \cos\phi_i \\ z = r \cdot \cos\theta_i \cdot \cos\phi_i \end{cases} \quad \text{Relation (7.1)}$$

[Math. 4]

$$\begin{cases} x = r \cdot \sin\phi_r \\ y = r \cdot \sin\theta_r \cdot \cos\phi_r \\ z = r \cdot \cos\theta_r \cdot \cos\phi_r \end{cases} \quad \text{Relation (7.2)}$$

A one-dimensional reflectance distribution function with an azimuth angle of incidence $\phi_i$ of zero degrees and an acceptance azimuth angle $\phi_r$ of zero degrees can also be calculated using a process similar to that described above. With the use of Relations (7.1) and (7.2), the conversion from angular coordinates to rectangular coordinates can be feasible.

In the process described above, the scattered light components caused by the structure whose size is on the order equal to or greater than the wavelength and the scattered light components caused by the structure whose size is on the order less than the wavelength are separated from each other. A threshold value for the separation may vary with the measurement accuracy of the surface-structure measurement unit 106. For example, scatter components caused by a structure whose size is on the order less than the limit of the measurement accuracy of the surface-structure measurement unit 106 may be estimated using the scattering model described above with respect to step S606. This process allows the estimation of a scattered light distribution including the geometrical-optics components and the wave-optics components even when the surface-structure measurement unit 106 has low measurement accuracy.

In the foregoing description, the process described above is performed by the measuring apparatus shown in FIG. 1. Alternatively, a portion of the process can be performed by an information processing apparatus such as a personal computer (PC) capable of executing various processing programs. The computation process may be performed using a dedicated hardware information processing apparatus.

Second Embodiment

Figure 13:
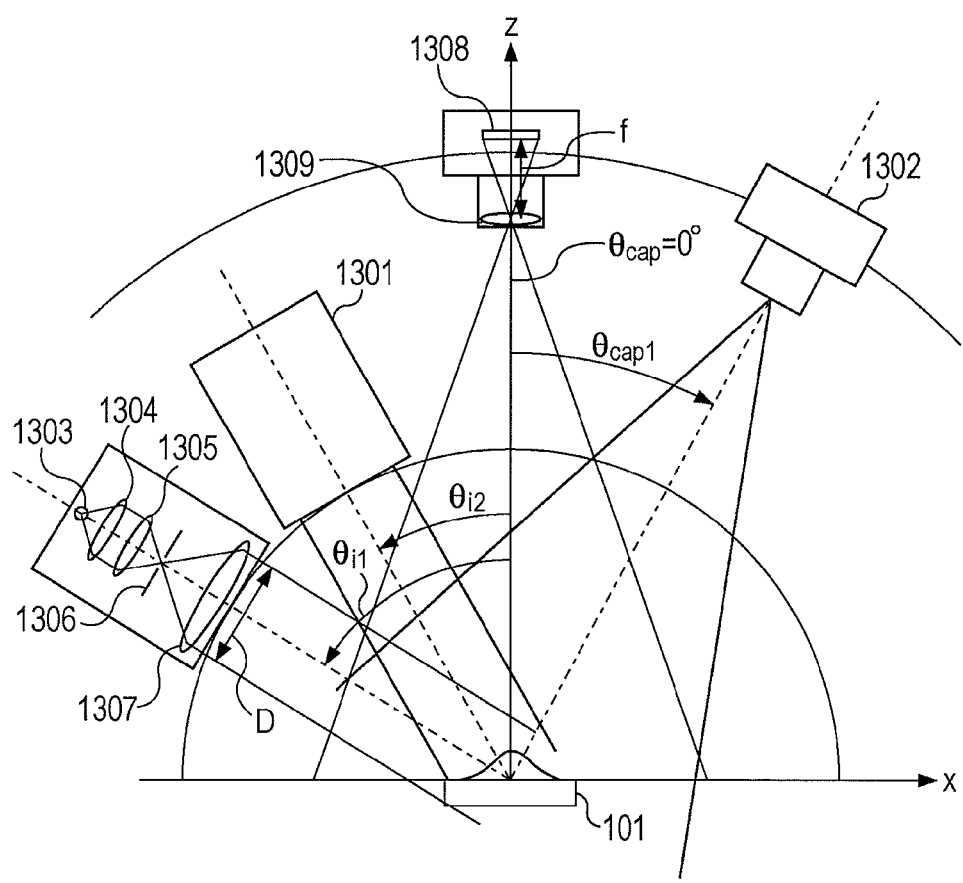
FIG. 13 is an external view of a measuring apparatus according to a second embodiment of the present invention.

FIG. 13 is an external view of a measuring apparatus according to a second embodiment of the present invention.

The measuring apparatus according to the present embodiment has functions of the reflected-light measurement unit 105 and the surface-structure measurement unit 106 of the first embodiment shown in FIG. 1. In other words, the measuring apparatus according to the present embodiment is configured to simultaneously measure shape data of the measurement target 101 and a scattered light distribution.

The measuring apparatus according to the present embodiment includes an illumination unit 1301 and a photodetector unit 1302. The illumination unit 1301 irradiates the measurement target 101 with illumination light, and the photodetector unit 1302 detects reflected light from the measurement target 101.

The illumination unit 1301 is configured as an afocal illumination unit. The illumination unit 1301 includes a point source 1303 configured to generate light, a collimator lens 1304, a front lens 1305, an aperture 1306, and a rear lens 1307. The point source 1303 includes an incandescent electric lamp, a halogen lamp, and a light emitting diode (LED). The illumination light radiated from the illumination unit 1301 is controlled by the diameter D of the aperture 1306 and parallel light is radiated. The illumination unit 1301 further includes a drive mechanism (not shown) and is movable at, for example, angles $\theta_{i1}$ and $\theta_{i2}$.

The photodetector unit 1302 includes an image sensor 1308 such as a complementary metal oxide semiconductor (CMOS) or charged-coupled device (CCD) sensor, and an imaging lens 1309. Like the illumination unit 1301, the photodetector unit 1302 further includes a drive unit (not shown) and is movable from, for example, a position given by $\theta_{cap}=0$ degrees to a position having an angle $\theta_{cap1}$.

Figure 14:
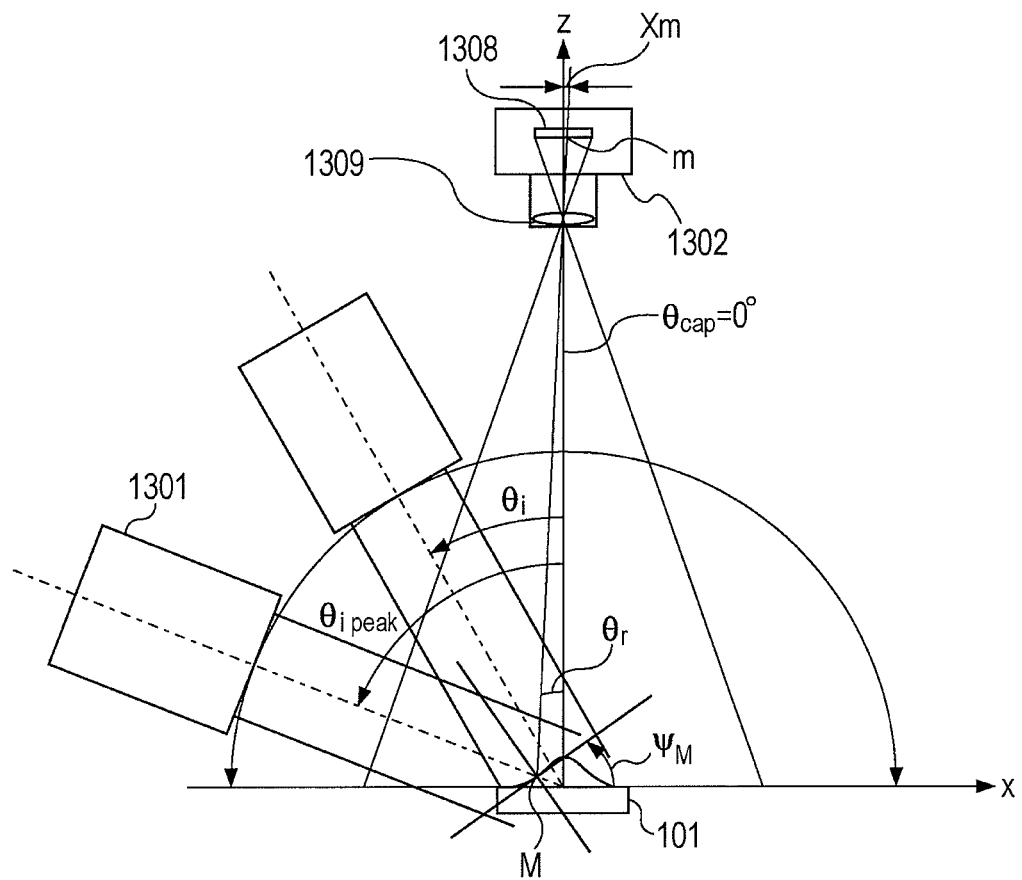
FIG. 14 is a diagram showing a method of measuring a surface structure of a measurement target according to the second embodiment.

The measurement of a surface structure of the measurement target 101 using the measuring apparatus shown in FIG. 13 will now be described. FIG. 14 is a diagram showing a method of measuring a surface structure according to the present embodiment. It is assumed that surface structural data at a measurement point M on the measurement target 101 is to be measured. A surface structure at the measurement point M has a structure whose size is on the order greater than the wavelength of the illumination light. In order to measure surface structural data, the photodetector unit 1302 measures reflected light.

If the photodetector unit 1302 has an image-capturing angle $\theta_{cap}$ of zero degrees, an image at the measurement point M on the measurement target 101 is formed at a position m on the image sensor 1308 using the imaging lens 1309 of the photodetector unit 1302. The position m is shifted by a value $X_m$ in the positive direction of the x axis with respect to the center of the image sensor 1308. While the image-capturing angle $\theta_{cap}$ of the photodetector unit 1302 is zero degrees, an angle of acceptance $\theta_r$ of the light at the image-forming position m is represented by Equation (8) as follows:

[Math. 5]

$$\theta_r = \tan^{-1}\left(\frac{X_m}{f}\right) \qquad \text{Equation (8)}$$

The photodetector unit 1302 measures a reflected light ray at every predetermined angle by changing the angle of incidence $\theta_i$ of illumination light from the illumination unit 1301 in steps of a predetermined angle from −90 degrees to 90 degrees while taking the angle of acceptance $\theta_r$ in Equation (8) into account.

Figure 15:
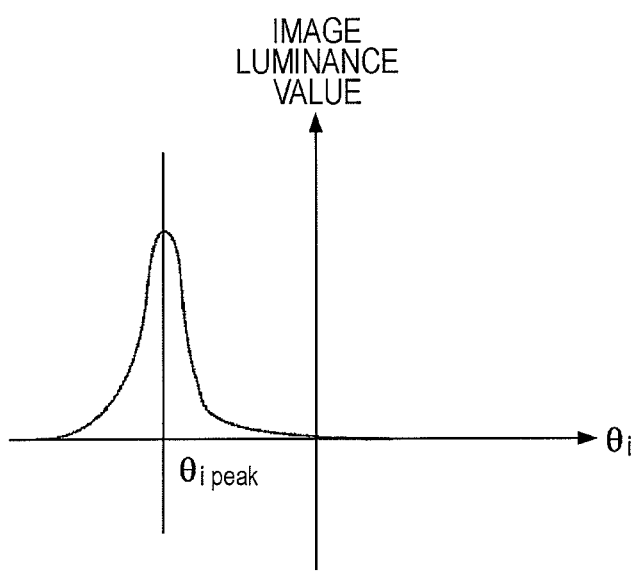
FIG. 15 is a diagram showing a luminance value of reflected light obtained by a photodetector unit.

FIG. 15 is a diagram showing a luminance value of reflected light obtained by the photodetector unit 1302.

When a luminance value at the image-forming position m is observed, as shown in FIG. 15, the luminance value is changed in steps of the angle and becomes maximum at a peak angle of incidence $\theta_{i\,peak}$.

It is considered that the luminance of an image is maximum when the angle of incidence $\theta_{i\,peak}$, the acceptance angle $\theta_r$, and a structural inclination angle $\Psi_M$ at the measurement point M satisfy the specular reflection conditions. Thus, the structural inclination angle $\Psi_M$ can be determined by Equation (9) as follows:

[Math. 6]

$$\psi_M = \frac{\theta_r + \theta_{ipeak}}{2} \qquad \text{Equation (9)}$$

This process is performed for an entire area of the measurement target 101 to compute structural inclination-angle data $\Psi(x)$ of the measurement target 101. The inclination-angle data $\Psi(x)$ may be converted into a shape inclination by computing the tangent of the inclination angle. Therefore, structural inclination data I(x) of the measurement target 101 is computed by Equation (10) as follows:

$$I(x) = \tan(\Psi(x)) \qquad \text{Equation (10)}$$

Since the structural data is an integral value of inclination, shape data G(x) is obtained by Equation (11) as follows:

$$G(x) = \int I(x) dx \qquad \text{Equation (11)}$$

Extending the procedure described above to a two-dimensional form yields data G(x, y) representing a three-dimensional structure.

Figure 16:
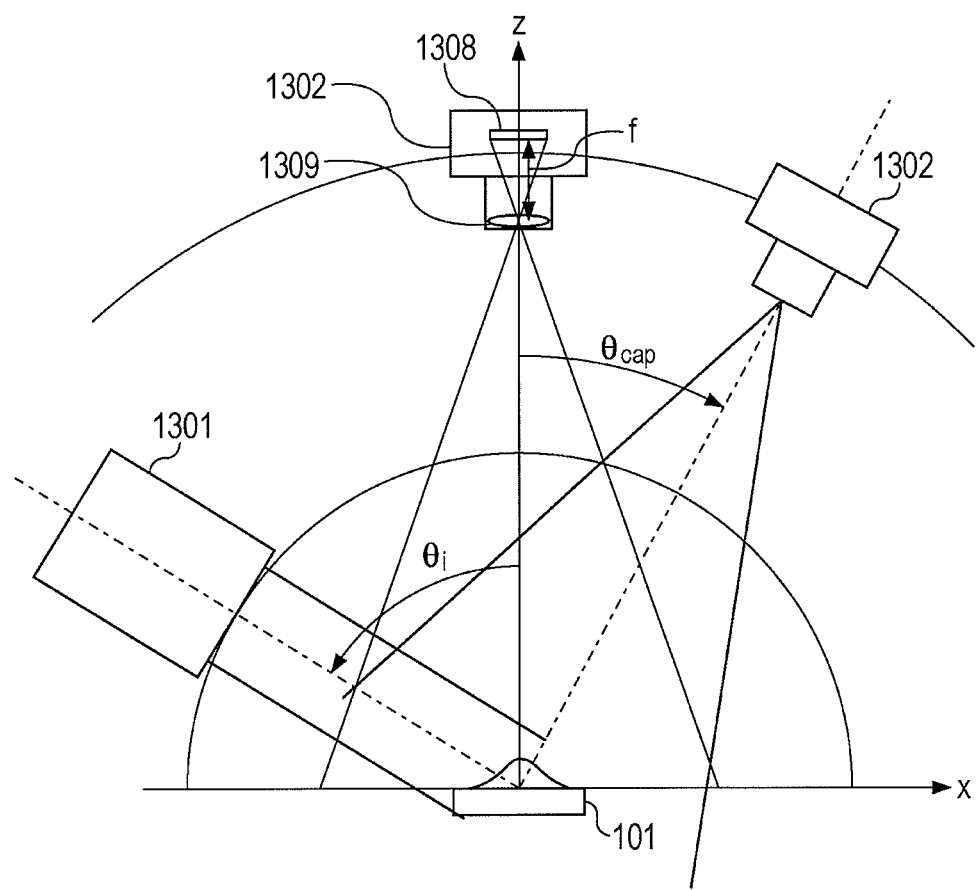
FIG. 16 is a diagram showing a method of measuring scatter characteristics according to the second embodiment.

The scattered light characteristic measurement of the measurement target 101 using the measuring apparatus shown in FIG. 13 will now be described. FIG. 16 is a diagram showing a method of measuring scattered light characteristics according to the present embodiment. In order to obtain scattered light characteristics, for example, the angles of incidence $\theta_i$ and $\phi_i$ of illumination light are fixed to predetermined values and the image-capturing angles $\theta_{cap}$ and $\phi_{cap}$ of the photodetector unit 1302 are varied from −90 degrees to +90 degrees. By doing so, scattered light angular characteristics can be obtained.

In this case, a resulting total luminance value of all pixels of the image can be equal to a total amount of light accepted at an angle of acceptance determined by the F value of the imaging lens 1309. Therefore, the total amount of light from a measurement target area can be computed using a total luminance value of pixels corresponding to the measurement target area that is being captured in the image.

Since taking a total luminance value of a specific area in a captured image by using the photodetector unit 1302 can be equivalent to the role of a photodetector unit in a goniophotometer, the function $F_{mea}(\theta_i, \phi_i, \theta_r, \phi_r)$ can be measured.

As compared to a goniophotometer, the above method allows selection of an area for which a total amount of light is to be taken while viewing the image, and allows measurement of a scattered light angular distribution without adding an amount of light from an unnecessary area.

In the measuring apparatus according to the present embodiment, therefore, with the use of the principle described above, structural data G(x, y) of a measurement target and a scattered light angular distribution $F_{mea}(\theta_i, \phi_i, \theta_r, \phi_r)$ can be simultaneously measured from image information.

The structural data and scattered light angular distribution obtained in the process described above are utilized in a process similar to the process according to the first embodiment shown in FIG. 6.

The invention claimed is:

1. An information processing apparatus for obtaining a scattered light distribution caused by wave-optics components from a reflected light comprising:
   a first obtaining unit configured to obtain a distribution of reflected light from a target to be measured;
   a second obtaining unit configured to obtain surface structure data of the target;
   a calculating unit configured to calculate a scattered light distribution caused by geometrical-optics of the reflected light, based on the surface structure data obtained by the second obtaining unit; and
   an output unit configured to output information regarding the scattered light distribution caused by the wave-optics from the reflected light, based on the scattered light distribution caused by the geometrical-optics calculated by the calculating unit.

2. The information processing apparatus according to claim 1, wherein the calculation is based on a luminance distribution of reflected light from the target when the target is irradiated with illumination light.

3. The information processing apparatus according to claim 1, wherein the calculation is based on smoothing measurement information regarding a surface structure of the target.

4. The information processing apparatus according to claim 1, wherein the calculation is based on a comparison of the geometrical-optics and the distribution of reflected light.

5. The information processing apparatus according to claim 1, wherein the calculation is based on a generated combined distribution comprising a combination of the geometrical-optics and a bell-shaped scattered light distribution.

6. The information processing apparatus according to claim 5, wherein the combined distribution is generated by changing the bell-shaped scattered light distribution.

7. An information processing method for obtaining a scattered light distribution caused by wave-optics components from a reflected light comprising:
   a first obtaining step of obtaining, by obtaining means, a distribution of reflected light from a target to be measured;
   a second obtaining step of obtaining surface structure data of the target;
   a calculating step of calculating, by calculating means, a scattered light distribution caused by geometrical-optics of the reflected light, based on the surface structure data obtained by the second obtaining step; and
   an output step of outputting, by output means, information regarding the scattered light distribution caused by the wave-optics from the reflected light, based on the scattered light distribution caused by the geometrical-optics calculated by the calculating step.

8. A non-transitory computer-readable storage medium on which is stored a program for causing a computer to function as:
- first obtaining means for obtaining a distribution of reflected light from a target to be measured;
- second obtaining means for obtaining surface structure data of the target;
- calculating means for calculating a scattered light distribution caused by geometrical-optics of the reflected light, based on the surface structure data obtained by the second obtaining means; and
- output means for outputting information regarding the scattered light distribution caused by the wave-optics from the reflected light, based on the scattered light distribution caused by the geometrical-optics calculated by the calculating means.

* * * * *